United States Patent [19]

Martel et al.

[11] 4,304,733

[45] Dec. 8, 1981

[54] NOVEL ALLETHROLONE DERIVATIVES

[75] Inventors: Jacques Martel, Bondy; Jean Tessier, Vincennes; André Téche, Nanterre, all of France

[73] Assignee: Roussel Uclaf, Paris, France

[21] Appl. No.: 141,200

[22] Filed: Apr. 17, 1980

[30] Foreign Application Priority Data

Apr. 26, 1979 [FR] France .................................. 79 10650

[51] Int. Cl.³ .................... C07C 121/48; C07C 69/74; C07C 35/06; A01N 37/08
[52] U.S. Cl. .................................. 260/464; 560/122; 560/124; 564/189; 568/807; 568/808; 568/838; 424/304; 424/305
[58] Field of Search .......................... 260/464, 557 R; 560/122; 568/807, 808, 838

[56] References Cited

U.S. PATENT DOCUMENTS 2,603,652 7/1952 Schechter et al. ................... 560/124
2,607,796 8/1952 Schechter et al. ................... 560/124
2,768,965 10/1956 Stansbury, Jr. et al. ..... 260/347.4 X
3,679,667 7/1972 Fanta .................................. 560/124
3,884,979 5/1975 Buchi ................................. 560/124

FOREIGN PATENT DOCUMENTS 874392 6/1979 Belgium .

Primary Examiner—Joseph Paul Brust
Attorney, Agent, or Firm—Hammond & Littell, Weissenberger & Muserlian

[57] ABSTRACT

Novel alcohols of the formula

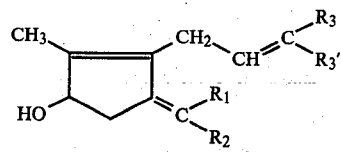

wherein $R_1$ and $R_2$ are individually selected from the group consisting of carbamoyl and $R_1'$ and $R_2'$, $R_1'$ and $R_2'$ are individually selected from the group consisting of hydrogen, halogen, alkyl of 1 to 6 carbon atoms, aryl of 6 to 10 carbon atoms, arylalkyl of 7 to 13 carbon atoms, alkoxycarbonyl of 2 to 5 carbon atoms and —CN and $R_3$ and $R_3'$ are individually selected from the group consisting of hydrogen, alkyl of 1 to 3 carbon atoms and alkenyl of 2 to 3 carbon atoms in the S form, R form or racemic mixtures thereof whose esters with cyclopropane carboxylic acids have an elevated insecticidal activity and their preparation.

10 Claims, No Drawings

NOVEL ALLETHROLONE DERIVATIVES

STATE OF THE ART

Esters of allethrolone with certain cyclopropane carboxylic acids are known to possess elevated insecticidal activity with a strong knock down activity but generally their lethal activity is less interesting. One example is dl allethrolone d trans chrysanthemate or bioallethrone. Also pertinent is Belgium Pat. No. 874,392.

OBJECTS OF THE INVENTION

It is an object of the invention to provide the novel alcohols of formula I and a novel process for their preparation.

These and other objects and advantages of the invention will become obvious from the following detailed description.

THE INVENTION

The novel compounds of the invention have the formula

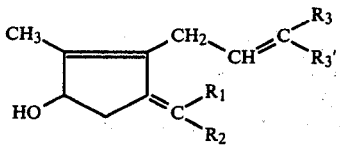

wherein $R_1$ and $R_2$ are individually selected from the group consisting of carbamoyl and $R_1'$ and $R_2'$, $R_1'$ and $R_2'$ are individually selected from the group consisting of hydrogen, halogen, alkyl of 1 to 6 carbon atoms, aryl of 6 to 10 carbon atoms, arylalkyl of 7 to 13 carbon atoms, alkoxycarbonyl of 2 to 5 carbon atoms and —CN and $R_3$ and $R_3'$ are individually selected from the group consisting of hydrogen, alkyl of 1 to 3 carbon atoms and alkenyl of 2 to 3 carbon atoms in the S form, R form or racemic mixtures thereof.

Examples of suitable substituents of $R_1'$ and $R_2'$ are fluorine, chlorine, bromine, methyl, ethyl, propyl, isopropyl, phenyl, naphthyl, benzyl, alkoxycarbonyl wherein the alkoxy may be methoxy, ethoxy, propoxy, isopropoxy, and branched or linear butoxy. Examples of $R_3$ and $R_3'$ are hydrogen, methyl, ethyl, propyl, isopropyl, vinyl, allyl and propen-1-yl.

Specific preferred compounds of formula I are 1S-hydroxy-2-methyl-3-allyl-4-methylene-cyclopent-2-ene, 1RS-hydroxy-2-methyl-3-(3-methyl-2-butenyl)-4-methylene-cyclopent-2-ene, 1S-hydroxy-2-methyl-3-allyl-4-dichloromethylene-cyclopent-2-ene, 1S-hydroxy-2-methyl-3-allyl-4-dicyanomethyllene-cyclopent-2-ene, 1S-hydroxy-2-methyl-3-allyl-4-ethylidene-cyclopent-2-ene, 1S-hydroxy-2-methyl-3-allyl-4E-benzylidene-cyclopent-2-ene, 1S-hydroxy-2-methyl-3-allyl-4-fluorochloromethylene-cyclopent-2-ene, 1S-hydroxy-2-methyl-3-allyl-4-cycanomethylene-cyclopent-2-ene and 1S-hydroxy-2-methyl-3-allyl-4-(cyanoethoxycarbonyl)-cyclopent-2-ene.

The novel process of the invention for the preparation of the alcohols of formula I comprises reacting in a solvent a compound of the formula

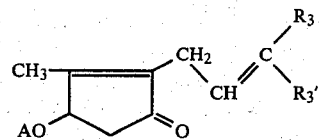

wherein $R_3$ and $R_3'$ have the above definition and A is selected from the group consisting of hydrogen, acyl of an aliphatic carboxylic acid of 2 to 6 carbon atoms, boric acid moiety and alkyl of 2 to 6 carbon atoms with a compound of the formula

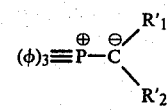

wherein $R_1'$ and $R_2'$ have the above definition and deblocking the hydroxyl when A is other than hydrogen with a desacylation agent or desetherication agent to obtain the corresponding compound of formula I when $R_1$ and $R_2$ are $R_1'$ and $R_2'$, and in the case where $R_1'$ and/or $R_2'$ is alkoxycarbonyl of 2 to 5 carbon atoms and the hydroxyl is blocked with a boric acid group or an acyl of an aliphatic carboxylic acid of 2 to 6 carbon atoms or an alkyl of 2 to 6 carbon atoms, reacting the product with ammonium hydroxide and then with a deblocking agent to obtain the compound of formula I when $R_1$ and/or $R_2$ are carbamoyl.

In the process of the invention, A of the compounds of formula II is preferably acetyl, propionyl, butyryl, valeryl, caproyl, boric acid residue or furanyl or pyranyl.

In an advantageous mode of the process of the invention, the compound of formula III is prepared by reacting a compound of the formula

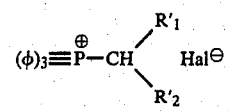

wherein $Hal^-$ is a halogen anion with a strong base selected from the group consisting of alkali metal hydrides, alkali metal amides, alkali metal alcoholates and alkyllithium in an organic solvent selected from the group consisting of ether, dimethylsulfoxide, tetrahydrofuran, dimethoxyethane, alkanols, monomethyl ether of diethylene glycol and diethyl ether of diethyleneglycol.

The optional blockage of the hydroxyl of the compound of formula II is preferably effected with an acylation agent such as an acid anhydride or acid halide in the presence of a tertiary base. The final deblocking of the hydroxyl may be effected with a desacylation agent such as a basic agent although the deblocking may be equally effected with boric acid. The blocking may also be effected with an ether group by the usual methods, especially with pyranyl or furanyl. The final deblocking of the hydroxyl group in this case may be effected in an acidic medium.

To prepare the compounds of formula I wherein $R_1$ and/or $R_2$ is carbamoyl, the compounds wherein $R_1$ and/or $R_2$ is alkoxycarbonyl are reacted with ammonia to obtain the corresponding carbamoyl compound.

When $R_1'$ and $R_2'$ of the compounds of formula III are halogen, it is preferred to form the compound of formula III in situ by reacting in a solvent in the presence of a strong base a haloform and triphenylphosphine. The strong base is preferably an alkali metal alcoholate and the solvent is preferably an aliphatic hydrocarbon such as heptane. In a general manner, the compounds of formula III are prepared in situ with a substituted triphenylmethylphosphonium halide such as the bromide or iodide.

A variation of the process of the invention for the preparation of a compound of formula I wherein $R_1$ is hydrogen and $R_2$ is cyano comprises reacting a compound of the formula

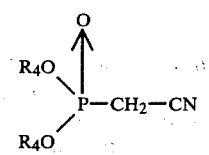

wherein $R_4$ is alkyl of 1 to 3 carbon atoms with a compound of formula II in an organic solvent in the presence of a strong base and deblocking the hydroxyl with a desacylation agent or a desetherification agent to obtain the desired compound of formula I. The strong base, organic solvent and deblocking agents may be the same as discussed above.

Another variation of the process of the invention to prepare a compound of formula I wherein $R_1$ and $R_2$ are individually selected from the group consisting of cyano and alkoxycarbonyl of 2 to 5 carbon atoms comprises reacting a compound of formula II wherein A is hydrogen with a compound of the formula $$R_1-CH_2-R_2 \qquad \text{III''}$$

to obtain the corresponding compound of formula I. The reaction is preferably effected in acetic acid in the presence of ammonium acetate.

The starting compounds of formula II are generally described in the literature. When $R_3$ and $R_3'$ are hydrogen, it is the ethers or esters of allethrolone or allethrolone itself. When $R_3$ and $R_3'$ are other than hydrogen, the compounds may be made by a process analogous to that described in the examples for the preparation of 1RS-hydroxy-2-methyl-3-(3-methyl-2-butenyl)-4-oxo-cyclopent-2-ene.

Allethrolone has been known for a long time to form esters with certain cyclopropane carboxylic acids having an elevated insecticidual activity shown by a strong knock down activity but their lethal activity has been less interesting such as bioallethrine or dl allethrolone d trans chrysanthemate. The alcohols of formula I of the invention form with numerous cyclopropane carboxylic acids esters having against insects an elevated knock down activity and a lethal activity which make the same esters particularly useful insecticides.

The insecticidal esters are described more fully in commonly assigned U.S. patent application Ser. No. 141,201 being filed on even date herewith and preferably have the formula

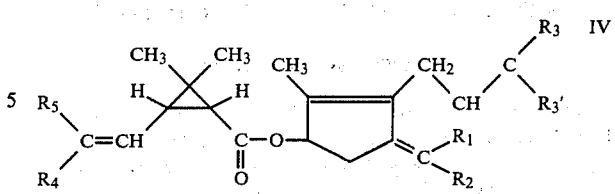

wherein $R_4$ and $R_5$ are individually selected from the group consisting of fluorine, chlorine and bromine or taken together with the carbon atoms to which they are attached form a hydrocarbon ring of 3 to 7 carbon atoms and $R_1$, $R_2$, $R_3$ and $R_3'$ have the above definition with the cyclopropane ring having a cis or trans, optically active or racemic configuration and the double bond in the 1-position of vinyl side chain may have the (E) or (Z) configuration. Other acids may also be used to form the esters.

The compounds of formula IV may be prepared by esterification of a compound of formula I or a functional derivative thereof such as its halide with an acid of the formula $$Y-OH \qquad \qquad V$$

wherein Y is a cyclopropane carboxylic acid as described above or a functional derivative thereof by known methods.

The compounds of formula IV are particularly effective against insects such as mosquitoes and houseflies with both a good knock down and lethal activity and are also effective against other diverse insects such as blatella, spodoptera, epilachna, tribolium, sitophilus and aphis.

In the following examples there are described several preferred embodiments to illustrate the invention. However, it should be understood that the invention is not intended to be limited to the specific embodiments.

EXAMPLE 1

1S-hydroxy-2-methyl-3-allyl-4-methylene-cyclopent-2-ene 31.4 g of potassium tert-butylate were added in 4 portions over 10 minutes to a stirred mixture of 250 ml of ether, 26.4 ml of tert.-butanol and 100 g of triphenylmethylphosphonium bromide under an inert atmosphere and the reaction mixture was allowed to stand at room temperature for 5 hours. The mixture was cooled to 0° to 5° C. and a solution of 31.9 g of 1S-hydroxy-2-methyl-3-allyl-4-oxo-cyclopent-2-ene in 30 ml of ether were added thereto over 20 minutes. The mixture was held at 0° to 5° C. for 2 hours and the temperature was raised to room temperature for 17 hours and the mixture was then poured into an aqueous saturated monosodium phosphate solution. The decanted aqueous phase was extracted with ether and the combined organic phases were dried over magnesium sulfate and evaporated to dryness. The residue was taken up in ether and the mixture was stirred a few minutes and was then filtered. The filtrate was evaporated to dryness under reduced pressure and the residue was chromatographed over silica gel. Elution with a 6-4 cyclohexane-ethyl acetate containing 2% of triethylamine yielded 26.05 g of 1S-hydroxy-2-methyl-3-allyl-4-methylene-cyclopent-2-ene. After crystallization from petroleum ether (B.p.=40°-70° C.), the product melted at 23° C. and had a specific rotation of $[\alpha]_D^{20} = -110° \pm 2°$ (c=0.8% in chloroform).

IR Spectrum (CHCl$_3$): Absorption at 3586 cm$^{-1}$ (OH); at 865 cm$^-$ (=CH$_2$); at 1637 cm$^{-1}$ (>C=C); at 916 cm$^{-1}$ (—CH=CH$_2$).

EXAMPLE 2

1RS-hydroxy-2-methyl-3-(3-methyl-2-butenyl)-4-methylenecyclopent-2-ene

STEP A: ETHYL 7-methyl-3-oxo-6-octenoate

A mixture of 1.4 g of ferric nitrate in 1200 ml of liquid ammonia was formed at −60° C. and was then stirred for 5 minutes after which 2 g of sodium were added thereto at −60° C. The mixture was stirred for 10 minutes and 104 g of sodium were added at −55±5° C. over 2½ hours. The mixture was stirred at −55° C. for one hour. 300 g of ethyl acetylacetate were added thereto over 30 minutes at less than −30° C. 1000 ml of ether at −20° C. were added to the mixture which was then stirred for 5 minutes. 289 g of 1-chloro-3-methyl-2-butene were added over 30 minutes at less than −25° C. and the mixture stood at room temperature for 17 hours. 1000 ml of ether were progressively added at less than ±15° C. followed by a solution of 250 ml of acetic acid in 1000 ml of water. The decanted aqueous phase was extracted with ether and the combined organic phases were washed with 2 N hydrochloric acid, then with water, dried over sodium sulfate and evaporated to dryness under reduced pressure. The residue was rectified under reduced pressure to obtain 175.5 g of ethyl 7-methyl-3-oxo-6-octenoate with a boiling point of 98° to 107° C. at 3 mmHg.

NMR Spectrum (CDCl$_3$-60 MHz: Peaks at 1.28 ppm (triplet J=7 Hz) and at 4.29 ppm (quadruplet J=7.5 Hz) (hydrogens of —COOC$_2$H$_5$); at 3.62 ppm (hydrogens of 2—CH$_2$—); at 1.64 ppm (doublet J=3 Hz) (hydrogens of 7-CH$_3$); at 5.08 ppm (6-hydrogen).

STEP B: 3-hydroxy-9-methyl-8-decene-2,5-dione 97 ml of 10 N sodium hydroxide solution were added over one hour at less than 33° C. to a suspension of 175 g of ethyl 7-methyl-3-oxo-6-octenoate in 875 ml of water and the mixture was stirred at room temperature for 20 hours and 25 ml of acetic acid were added thereto to obtain a pH of 7. An aqueous solution containing 396 g of pyruvaldehyde (16.8% by weight) was added to the mixture at 20° to 25° C. while maintaining a pH of 7 and the mixture was stirred for 20 hours at room temperature during which 30 ml of acetic acid were added to keep the pH at 7. 1000 ml of methylene chloride were added thereto and the mixture was stirred for 10 minutes. The decanted aqueous phase was extracted with methylene chloride and the combined organic phases were dried over sodium sulfate and evaporated to dryness under reduced pressure to obtain 175 g of 3-hydroxy-9-methyl-8-decene-2,5-dione.

STEP C: 1RS-hydroxy-2-methyl-3-(3-methyl-2-butenyl)-4-oxocyclopent-2-ene

Nitrogen was bubbled through 875 ml of 1 N sodium hydroxide solution for one hour and then 175 mg of hydroquinone were added thereto at 3° C. 175 g of 3-hydroxy-9-methyl-8-decene-2,5-dione were added to the mixture over one hour at 2°±1° C. and the mixture was stirred for 2½ hours at that temperature. Then, 80 ml of concentrated hydrochloric acid were added with stirring and the mixture was stirred for 30 minutes during which the temperature rose to 20° C. 200 g of sodium chloride were added to the mixture which was then stirred for 10 minutes. 1000 ml of methylene chloride were added thereto and the decanted aqueous phase was extracted with methylene chloride. The combined organic phases were dried over sodium sulfate and evaporated to dryness under reduced pressure. The residue was rectified under reduced pressure to obtain 53.4 g of 1RS-hydroxy-2-methyl-3-(3-methyl-2-butenyl)-4-oxo-cyclopent-2-ene with a boiling point of 143° to 148° C. at 0.5 mmHg.

NMR Spectrum (CDCl$_3$-60 MHz): Peaks at 1.72 ppm (hydrogens of —CH$_3$ of side chain); at 2.87 ppm (doublet-J=7 Hz) (1-hydrogens of side chains); at 4.7 ppm (α-hydrogen of OH); at 5.03 ppm (triplet-J=7 Hz) (2-hydrogen of side chain); at 2.67 ppm (hydrogen of —OH); at 2.08 to 2.92 ppm (4=CH$_2$ of cyclopentene).

STEP D: 1RS-hydroxy-2-methyl-3-(3-methyl-2-butenyl)-4-methylene-cyclopent-2-ene 9.93 g of potassium tert.-butylate were added in 6 fractions over 30 minutes to a stirred suspension of 29.7 g of triphenylmethylphosphonium bromide, 100 ml of ether and 7.84 ml of tert.-butanol and the reaction mixture was stirred at 20° C. under an inert atmosphere for 5 hours. The mixture was cooled to 0° C. and a solution of 10 g of 1RS-hydroxy-2-methyl-3-(3-methyl-2-butenyl)-4-oxo-cyclopent-2-ene in 10 ml of ether was added thereto over 20 minutes. The mixture was stirred at 0° C. under an inert atmosphere for 17 hours and after allowing the temperature to rise to 20° C., the mixture was stirred for another 3 hours and was then poured into an aqueous saturated monosodium phosphate solution. The mixture was stirred for 15 minutes and the decanted aqueous phase was extracted with ether. The combined organic phases were dried over magnesium sulfate, filtered and evaporated to dryness under reduced pressure. The residue was taken up in ether and the mixture was stirred at 0° C. for 10 minutes and was vacuum filtered. The recovered product was washed with ether. The combined filtrates were evaporated to dryness under reduced pressure to obtain 19.54 g of raw product which was chromatographed over silica gel. Elution with a 7-3 benzene-ethyl acetate mixture containing 1% triethylamine yielded 7.244 g of 1RS-hydroxy-2-methyl-3-(3-methyl-2-butenyl)-4-methylene-cyclopent-2-ene with an Rf=0.55.

IR Spectrum (chloroform): Absorption complex at 3605-3580 cm$^{-1}$ characteristic of OH; at 1630 cm$^{-1}$ (C=C); at 865 cm$^{-1}$ (=CH$_2$).

NMR Spectrum (CDCl$_3$-60 MHz): Peaks at 1.7 ppm (hydrogens of —CH$_3$ on side chain); at 1.83 ppm (hydrogens of 2-CH$_3$); at 1.98 ppm (hydrogen of 1-OH); at 2.83 to 2.95 ppm (1-hydrogens of side chain); at 5.03 ppm (triplet-J=7 Hz) (3-hydrogens of side chain); at 4.42 to 4.83 ppm (α-hydrogen of OH and 4—=CH$_2$).

EXAMPLE 3

1S-hydroxy-2-methyl-3-allyl-4-dichloromethylene-cyclopent-2-ene

STEP A: 1S-acetoxy-2-methyl-3-allyl-4-oxo-cyclopent-2-ene 9.15 ml of triethylamine and 3.1 ml of acetic acid anhydride were added to a solution of 2 g of 1S-hydroxy-2-methyl-3-allyl-4-oxo-cyclopent-2-ene in 15 ml of methylene chloride and after 30 minutes of reaction, the mixture was poured into an aqueous saturated monosodium phosphate solution. The mixture was extracted with ether and the organic phase was washed with water, dried over magnesium sulfate and filtered.

The filtrate was evaporated to dryness to obtain 3.049 g of 1S-acetoxy-2-methyl-3-allyl-4-oxo-cyclopent-2-ene.

NMR Spectrum (CDCl$_3$-90 MHz): Peaks at 1.67 and 2.02 ppm (hydrogens of 2—CH$_3$ and 1-acetoxy); at 2.11 to 3.01 ppm (hydrogens of 5-position of ring and 1-position of side chain); at 4.94 to 5.09 ppm (hydrogens of side chain); at 5.55 to 6 ppm (2-hydrogen of side chain).

STEP B: 1S-acetoxy-2-methyl-3-allyl-4-dichloromethylene-cyclopent-2-ene

A mixture of 111 g of ground triphenyl phosphine, 1000 ml of heptane, 60 ml of tert.-butanol and 70.8 g of potassium tert.-butylate was stirred at room temperature and after cooling to $-20°$ C., a solution of 75.6 g of chloroform and 60 ml of heptane were added thereto with stirring over 90 minutes. The mixture was stirred at $-20°$ C. for 5 hours and then stood at $-20°$ C. for 17 hours to obtain an ylide solution, a portion of which was kept at $-20°$ C. under nitrogen. A solution of 26 g of 1S-acetoxy-2-methyl-3-allyl-4-oxo-cyclopent-2-ene in 140 ml of tetrahydrofuran was added with stirring at $-20°$ C. under an inert atmosphere to the rest of the ylide solution and after the temperature rose to room temperature, the mixture was stirred at room temperature for 5 hours. The first part of the ylide solution was added to the mixture at $-20°$ C. and the temperature rose again to 20° C. The mixture was stirred for 17 hours at 20° C. under an inert atmosphere and was then filtered. The filtrate was added to an aqueous saturated monosodium phosphate solution and the mixture was extracted with ether. The combined organic phases were dried over sodium sulfate, filtered and evaporated to dryness under reduced pressure. The residue was chromatographed over silica gel and was eluted with an 8-2 benzene-ethyl acetate mixture containing 1% triethylamine to obtain 14 g of 1S-acetoxy-2-methyl-3-allyl-4-dichloromethylene-cyclopent-2-ene with an Rf=0.5.

STEP C: 1S-hydroxy-2-methyl-3-allyl-4-dichloromethylene-cyclopent-2-ene

A solution of 9.3 g of sodium carbonate in 195 ml of water and a little dioxane was added with stirring to a solution of 14 g of the product of Step B in 350 ml of ethanol and the mixture was stirred at 20° C. for 4 hours and was evaporated to dryness. The residue was taken up in water and the solution was extracted with isopropyl ether. The combined organic phases were dried over sodium sulfate, filtered and evaporated to dryness under reduced pressure to obtain 10.9 g of 1S-hydroxy-2-methyl-3-allyl-4-dichloromethylene-cyclopent-2-ene.

IR Spectrum (chloroform): Absorption at 3600–3587 cm$^{-1}$ (—OH); at 1635–1600 cm$^{-1}$ (—C=C)

NMR Spectrum (CDCl$_3$,60 MHz): Peaks at 1.77 to 3.17 ppm (5-hydrogens of ring); at 1.83 ppm (2—CH$_3$ of ring); at 3.27 ppm (doublet J=7 Hz) (1-hydrogens of side chain); at 4.5 to 4.67 ppm (1-hydrogen of ring); at 4.83 to 5.25 ppm (hydrogens of side chain); at 5.5 to 6.33 ppm (2-hydrogens of side chain).

EXAMPLE 4

1S-hydroxy-2-methyl-3-allyl-4-ethylidene-cyclopent-2-ene 4 g of boric acid were added to a mixture of 30 g of 1S-hydroxy-2-methyl-3-allyl-4-oxo-cyclopent-2-ene in 200 ml of benzene and the mixture was refluxed for 5 hours after which 140 ml of benzene were distilled under reduced pressure. The mixture was concentrated to dryness under reduced pressure and the residue was taken up on sufficient benzene for a total volume of 100 ml. A mixture of 68 g of triphenylethyl phosphonium bromide, 250 ml of ether and 18 ml of tert.-butanol was prepared and 20 g of potassium tert.-butylate were added thereto in 3 portions at 0° to 5° C. after which the mixture was stirred for 4 hours. Then, the benzene solution was slowly added thereto at 0° to 5° C. and the mixture was stirred at 20° C. for 17 hours and then was poured into an iced aqueous saturated ammonium chloride solution. The decanted aqueous phase was extracted with ether and the combined organic phases were washed with aqueous sodium chloride, dried and evaporated to dryness. The residue was taken up in 250 ml of isopropyl ether and the mixture was stirred at 20° C. for 2 hours and was then filtered. The filtrate was evaporated to dryness and the residue was chromatographed over silica gel. Elution with a 7-3 cyclohexane-ethyl acetate mixture containing 1% triethylamine yielded 6.2 g of 1S-hydroxy-2-methyl-3-allyl-4-oxo-cyclopent-2-ene with a specific rotation of $[\alpha]_D^{20} = -126.5° \pm 2.5°$ (c=1% in ethanol).

IR Spectrum (chloroform): Absorption at 1608 cm$^{-1}$ (conjugated C=C); towards 3585 cm$^{-1}$ (complexed OH).

NMR Spectrum (CDCl$_3$-60 MHz): Peaks at 2.08 to 3.17 ppm (5-hydrogens); at 1.8 ppm (hydrogens of 2—CH$_3$); at 4.55 and 4.63 ppm (1-hydrogen); at 2.08 to 3.16 ppm (1-hydrogens of allyl); at 4.83 to 6.1 ppm (other hydrogens of allyl and 1-hydrogen of ethylidene); at 1.6 and 1.71 ppm (2-hydrogens of ethylidene).

1S-hydroxy-2-methyl-3-allyl-4-ethylidene-cyclopent-2-ene was also prepared using the procedure of Example 1 beginning with triphenylethylphosphonium bromide.

EXAMPLE 5

1S-hydroxy-2-methyl-3-allyl-4-(E)-benzylidene-cyclopent-2-ene 90 ml of tert.-butanol were added to a mixture of 22 g of potassium tert.-butylate in 250 ml of tetrahydrofuran and 76.4 g of triphenylbenzylphosphonium bromide were slowly added thereto. The mixture was stirred at 23° C. for one hour and then a solution of 29.8 g of 1S-hydroxy-2-methyl-3-allyl-4-oxo-cyclopent-2-ene in 10 ml of tetrahydrofuran was slowly added thereto. The mixture was refluxed for 24 hours and cooled to 20° C. and poured into an aqueous saturated monosodium phosphate solution. The mixture was extracted with ether and the ether extracts were washed with water, dried and evaporated to dryness to obtain 81.5 g of raw product. The latter was chromatographed over silica gel and was eluted with a 1-1 cyclohexane-ethyl acetate mixture to obtain 25.5 g of 1S-hydroxy-2-methyl-3-allyl-4(E)-benzylidene-cyclopent-2-ene melting at <50° C.

IR Spectrum (chloroform): Absorption at 3600 cm$^{-1}$ (OH); at 1635–1625 cm$^{-1}$ (conjugated system); at 1597–1488 cm$^{-1}$ (aromatic bands); at 999–914 cm$^{-1}$ (allyl).

NMR Spectrum(CDCl$_3$-60 MHz): Peaks at 4.66 ppm (1-hydrogen); at 1.89 ppm (hydrogens of 2-CH$_3$); at 3.03 and 3.12 ppm (1-hydrogens of allyl chain); at 4.83 to 5.25 ppm (3-hydrogens of allyl chain); at 5.55 to 6.16 ppm (2-hydrogens of allyl chain); at 6.28 ppm (hydrogen of benzylidene); at about 7.32 ppm (aromatic hydrogens).

EXAMPLE 6

1S-hydroxy-2-methyl-3-allyl-4-fluorochloromethylene-cyclopent-2-ene

STEP A: 1S-acetoxy-2-methyl-3-allyl-4-fluorochloromethylene-cyclopent-2-ene

A mixture of 100 ml of n-heptane, 6.8 g of potassium tert.-butylate and 5.7 ml of tert.-butanol formed at 20° C. was heated at 50° C. for 15 minutes and then a mixture of 15.75 g of triphenylphosphine in 10 ml of n-heptane was added thereto at 20° C. The mixture was cooled to 0° C. and a solution of 7.72 g of dichlorofluoromethane in 75 ml of n-heptane was slowly added thereto. A solution of 9.71 g of 1S-acetoxy-2-methyl-3-allyl-4-oxo-cyclopent-2-ene in 10 ml of tertrahydrofuran was slowly added to the mixture at 0° C. and the mixture was then stirred at 20° C. for 4 hours and then one hour at 50° C. The mixture was evaporated to dryness under reduced pressure and the residue was taken up in ether. The solution was filtered and the filtrate was washed with aqueous saturated monosodiumphosphate solution, with water, dried and filtered. The filtrate was evaporated to dryness and the 10 g of raw oil was chromatographed over silica gel. Elution with a 95-5 cyclohexane-ethyl acetate mixture containing 1% triethylamine yielded 6.75 g of 1S-acetoxy-2-methyl-3-allyl-4-fluorochloromethylene-cyclopent-2-ene.

IR Spectrum (chloroform): Absorption at 1728 cm$^{-1}$

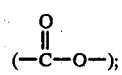

at 1669-1583 cm$^{-1}$ (conjugated system); at 990-919 cm$^{-1}$(—CH=CH$_2$).

STEP B: 1S-hydroxy-2-methyl-3-allyl-4-fluorochloromethylene-cyclopent-2-ene

A solution of 4.5 g of sodium carbonate in 90 ml of water and 20 ml of dioxane was added to a mixture of 6.5 g of the product of Step A in 150 ml of ethanol and the mixture was stirred at 20° C. for 50 hours. The mixture was evaporated to dryness and the residue was taken up in 200 ml of water. The aqueous solution was extracted with isopropyl ether and the organic phase was dried and evaporated to dryness. The residue was chromatographed over silica gel and was eluted with a 85-15 toluene-ethyl acetate mixture containing 1% triethylamine to obtain 2.5 g of 1S-hydroxy-2-methyl-3-allyl-4-fluorochloromethylene-cyclopent-2-ene with a specific rotation of $[\alpha]_D^{20} = -16.5° \pm 2°$ (c=0.55% in benzene).

Analysis: C$_{10}$H$_{12}$ClFO; molecular weight=202.66:
Calculated: %C 59.26; %H 5.96; %Cl 17.49; %F 9.37. Found: %C 59.2; %H 6.0; %Cl 17.7; %F 9.4.

IR Spectrum (chloroform): Absorption at 3600 cm$^{-1}$(OH); at 1668-1635 cm$^{-1}$ (conjugated C=C); at 990-918 cm$^{-1}$ (CH=CH$_2$).

NMR Spectrum (CDCl$_3$-60 MHz): Peaks at 4.43 ppm (1-hydrogen); at 1.8 ppm (hydrogens of 2—CH$_3$); at 2.17 to 3.33 ppm (1-hydrogens of allyl); at 5.5 to 6.5 ppm (2-hydrogen of allyl); at 4.8 to 5.3 ppm (3-hydrogens of allyl); at 2.17 to 3.33 ppm (5-hydrogens).

EXAMPLE 7

1S-hydroxy-2-methyl-3-allyl-4-cyanomethylene-cyclopent-2-ene 19.4 ml of O,O-diethyl cyanomethylphosphonate were slowly added to a mixture of 4.8 g of sodium hydride as a 50% mineral oil suspension in 200 ml of monoglyme and the mixture was stirred for 30 minutes and was then cooled to 5° C. A mixture of 15.22 g of 1S-hydroxy-2-methyl-3-allyl-4-oxo-cyclopent-2-ene in 20 ml of monoglyme was added to the mixture over 20 minutes and the mixture was stirred at 5° C. for 15 minutes and then at 20° C. for 20 hours. The mixture was evaporated to dryness under reduced pressure and the residue was added to a mixture of 100 ml of N hydrochloride acid and 200 ml of water at 5° C. The mixture was extracted with ether and the organic phase was dried and evaporated to dryness to obtain 18 g of residue. The latter was chromatographed over silica gel and was eluted with a 95-5 methylene chloride-ethyl acetate mixture and then with a 6-4 toluene-ethyl acetate mixture to obtain 8.76 g of 1S-hydroxy-2-methyl-3-allyl-4-cyanomethylene-cyclopent-2-ene with a specific rotation of $[\alpha]_D^{20} = -140° \pm 3°$ (c=0.42% in benzene).

Analysis: C$_{11}$H$_{13}$NO; molecular weight=175.23:
Calculated: %C 75.39; %H 7.47; %N 7.99. Found: %C 75.3; %H 7.5; %N 7.8.

IR Spectrum (chloroform): Absorption at 3600 cm$^{-1}$ (OH); at 2205 cm$^{-1}$ (conjugated —CN); at 1636 and 1611 cm$^{-1}$(conjugated C=C); at 990 and 919 cm$^{-1}$ (—CH=CH$_2$ deformation).

NMR Spectrum (CDCl$_3$-60 MHz): Peaks at 2.33 to 3.5 ppm (5-hydrogens); at 4.72 ppm (1-hydrogen); at 1.93 ppm (hydrogens of 2—CH$_3$); at 2.33 to 3.5 ppm (1-hydrogens of allyl chain); at 5.42 to 6.08 ppm (2-hydrogen of allyl); at 4.75 to 5.33 ppm (3-hydrogens of allyl and hydrogen of cyanomethylene).

EXAMPLE 8

1S-hydroxy-2-methyl-3-allyl-4-(cyanoethoxycarbonyl)-methylene-cyclopent-2-ene A mixture of 3.1 g of 1S-hydroxy-2-methyl-3-allyl-4-oxo-cyclopent-2-ene, 4.52 g of ethyl cyanoacetate, 0.7 g of ammonium acetate, 1 ml acetic acid and 50 ml of toluene was refluxed for 6 hours and the water was distilled. The mixture was cooled to 20° C. and 0.6 g of ammonium acetate in 1 ml of acetic acid were added thereto. The mixture was refluxed for another 6 hours and the water of reaction was distilled. The mixture was cooled to 20° C. and was diluted with ether. The decanted ether phase was washed with water, dried and evaporated to dryness to obtain 4.15 g of residue. The latter was chromatographed over silica gel and was eluted with a 6-4 benzene-ethyl acetate mixture to obtain 1.06 g of 1S-hydroxy-2-methyl-3-allyl-4-(cyanoethoxycarbonyl)methylenecyclopent-2-ene with a specific rotation of $[\alpha]_D^{20} = -87° \pm 2°$ (c=0.9% in chloroform).

IR Spectrum (chloroform): Absorption at 3600 cm$^{-1}$ (OH); at 2220 cm$^{-1}$ (—CN); at 1718 cm$^{-1}$

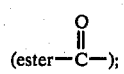

at 1637, 1616 and 1507 cm$^{-1}$ (—C=C—conjugated); at 990-918 cm$^{-1}$ (—CH=CH$_2$ deformation).

NMR Spectrum (CDCl$_3$-60 MHz): Peaks at 1.22, 1.33, 1.45, 4.11, 4.23, 4.35 and 4.47 ppm (—COOCH$_2$CH$_3$); at 2.06 ppm (hydrogens of 2-CH$_3$); at 2.58 ppm (hydrogen of —OH); at 2.75 to 4 ppm (5-hydrogens); at 3.42 to 3.53 ppm (1-hydrogens of allyl chain); at 4.75 ppm (1-hydrogen); at 4.66 to 5.25 ppm (3-hydrogens of allyl chain); at 5.67 and 6.25 ppm (2-hydrogen of allyl chain).

EXAMPLE 9

1S-hydroxy-2-methyl-3-allyl-4-dicyanomethylene-cyclopent-2-ene

Using the procedure of Example 8, 45 g of 1S-hydroxy-2-methyl-3-allyl-4-oxo-cyclopent-2-ene and 24 g of malonitrile were reacted and the residue was chromatographed over silica gel. Elution with a 6-4 toluene-ethyl acetate mixture and then with an 8-2 toluene-ethyl acetate mixture yielded 34.9 g of 1S-hydroxy-2-methyl-3-allyl-4-dicyanomethylene-cyclopent-2-ene with a specific rotation of $[\alpha]_D^{20} = -203° \pm 4°$ (c=0.5% in benzene).

Analysis: C$_{12}$H$_{12}$N$_2$O; Calculated: %C 71.98; %H 6.04; %N 13.99. Found: %C 71.8; %H 6.2; %N13.8.

IR Spectrum (chloroform): Absorption at 3600 cm$^{-1}$ (OH); at 2222 cm$^{-1}$ (—CN); at 1637, 1611 and 1567 cm$^{-1}$ (conjugated—C═C—); at 990 and 920 cm$^{-1}$ (—CH═CH$_2$ deformation).

NMR Spectrum (CDCl$_3$-60 MHz): Peaks at 4.75 ppm (1-hydrogen); at 2.58 ppm (hydrogen of —OH); at 2.07 ppm (hydrogens of 2-CH$_3$); at 3.25 to 3.42 ppm (1-hydrogens of allyl); at 5.5 to 6.25 ppm (2-hydrogen of allyl); at 4.67 to 5.25 ppm (3-hydrogens of allyl).

EXAMPLE 10

(1S) 2-methyl-3-allyl-4-methylene-cyclopent-2-ene-1-yl, 2,2-dimethyl-3S-(2,2-difluoroethenyl)-cyclopropane-1R-carboxylate A solution of 3.88 g of 2,2-dimethyl-3S-(2,2-difluoroethenyl)-cyclopropane-1R-carboxylic acid chloride in 5 ml of benzene was added with stirring below 30° C. to a suspension of 3 g of the product of Example 1 in 30 ml of benzene and 4.5 ml of pyridine and the mixture was stirred at 20° C. for 4 hours and was then poured into water. The decanted aqueous phase was extracted with isopropyl ether and the combined organic phases were washed with water, dried over sodium sulfate and filtered. The filtrate was evaporated to dryness under reduced pressure to obtain 2.3 g of pure (1S) 2-methyl-3-allyl-4-methylene-cyclopent-2-ene-1-yl 2,2-dimethyl-3S-(2,2-difluoroethenyl)-cyclopropane-1R-carboxylate with a boiling point of 113°–114° C. at 0.1 mm Hg and a specific rotation of $[\alpha]_D^{20} = -67° \pm 2.5°$ (c=0.6% in benzene).

Analysis: C$_{18}$H$_{22}$F$_2$O$_2$; Calculated: %C 70.11; %H 7.19; %F 12.32. Found: %C 69.8; %H 7.2; %F 12.5.

IR Spectrum (chloroform): Absorption at 1746–1716 cm$^{-1}$ (—C═O and ═CF$_2$); at 1636 cm$^{-1}$ (—C═C of cyclopentene and ═CH$_2$); at 920–991 cm$^{-1}$ (—CH═CH$_2$).

EXAMPLE 11

(1S) 2-methyl-3-allyl-4-methylene-cyclopent-2-ene-1-yl 2,2-dimethyl-3S-(2,2-dichloroethenyl)-cyclopropane-1R-carboxylate A solution of 7 g of 2,2-dimethyl-3S-(2,2-dichloroethenyl)-cyclopropane-1R-carboxylic acid chloride in 5 ml of benzene was added over 15 minutes to a solution of 440 g of the product of Example 1 in 15 ml of benzene and 2.6 ml of pyridine and the mixture was stirred for 17 hours. 20 ml of water were added thereto and the mixture was stirred for 5 minutes. The decanted aqueous phase was extracted with benzene and the organic phase was washed with water. The wash waters were extracted with benzene and the combined organic phases were dried over magnesium sulfate and filtered and the filtrate was evaporated to dryness under reduced pressure. The residual oil was chromatographed over silica gel and was eluted with a 95-5 cyclohexane-ethyl acetate mixture containing 1% triethylamine to obtain 6.99 g of (1S) 2-methyl-3-allyl-4-methylene-cyclopent-2-ene-1-yl 2,2-dimethyl-3S-(2,2-dichloroethenyl)-cyclopropane-1R-carboxylate with an Rf =0.58 and a specific rotation of $[\alpha]_D^{20} = -45.5° \pm 1.5°$ (c=1% in ethanol).

Analysis: C$_{18}$H$_{22}$O$_2$Cl$_2$: Calculated: %C 63.35; %H 6.49; %Cl 20.77. Found: %C 63.3; %H 6.6; %Cl 20.3.

IR Spectrum (chloroform): Absorption at 1717 cm$^{-1}$ (C═O); at 1633–1618 cm$^{-1}$ (C═C); at 990–917 cm$^{-1}$ (—CH═CH$_2$).

EXAMPLE 12

(1S) 2-methyl-3-allyl-4-methylene-cyclopent-2-ene-1-yl 2,2-dimethyl-3R-cyclopentylidene-methyl-cyclopropane-1R-carboxylate A solution of 7.08 g of 2,2-dimethyl-3R-cyclopentylidenemethyl-cyclopropane-1R-carboxylic acid chloride in 3 ml of benzene was added over 10 minutes at 28° C. to a suspension of 5 g of the product of Example 1 in 15 ml of benzene and 2.96 ml of pyridine and the mixture was stirred at 20° C. for 17 hours. 20 ml of water were added to the mixture which was then stirred for 10 minutes and the decanted aqueous phase was extracted with benzene. The combined organic phases were washed with water and the wash waters were extracted with benzene. The combined organic phases were dried over magnesium sulfate and filtered and the filtrate was evaporated to dryness under reduced pressure. The residue was chromatographed over silica gel and was eluted with a 95-5 cyclohexane-ethyl acetate mixture containing 1% triethylamine to obtain 8.24 g of (1S) 2-methyl-3-allyl-4-methylene-cyclopent-2-ene-1-yl 2,2-dimethyl-3R-cyclopentylidene-methyl-cyclopropane-1R-carboxylate with an RF =0.55 and a specific rotation of $[\alpha]_D^{20} = -87° \pm 1°$ (c=0.9% in ethanol).

IR Spectrum (chloroform): Absorption at 1715 cm$^{-1}$ (>C═O); at 1635 cm$^{-1}$ (—C═C—); at 865 cm$^{-1}$ (>C═CH$_2$).

INSECTICIDAL ACTIVITY

A. Knock down Activity against Houseflies

The compounds tested were (1S)-2-metyl-3-allyl-4-methylene-cyclopent-2-ene-1-yl 2,2-dimethyl-3R-cyclopentylidenemethyl-cyclopropane-1R-carboxylate (compound A) and (1S) 2-methyl-3-allyl-4-methylene-cyclopent-2-ene-1-yl 2,2-dimethyl-3S-(2,2-difluoroethenyl)-cyclopropane-1R-carboxylate (compound B).

The test compounds dissolved in equal volumes of acetone and kerosene were directly sprayed on the insects in a Kearns and March chamber with a volume of 2×0.2 ml. 50 insects were used in each test and readings were taken 2,4,6, 8, 10 and 15 minutes after the spraying and compared to controls to determine KT$_{50}$. For compound A without piperonyl butoxide synergist, the KT$_{50}$ was 11 minutes and with a synergist 9.5 minutes. For compound B without a synergist, the KT$_{50}$ was 3.6 minutes as compared to a $KT_{50}$ for bioallethrine under the same conditions of 9.8 minutes.

B. Lethal Activity against Houseflies

1 μl of an acetone solution of the test compounds were applied topically to the dorsal thorax of houseflies with an Arnold micromanipulator and the number of dead insects was determined 24 hours later. The tests were effected without and with 10 parts by weight of piperonyl butoxide per part by weight of test compound and $DL_{50}$ (dose in nanograms to kill 50% of the insects) was determined. The $DL_{50}$ was 5.19 nanograms per insect for compound A and for compound B 2.7 nanograms per insect without synergist and 2.8 with the synergist.

C. Lethal Activity against *Aedes Aegypti*

This test was the O.M.S. method wherein 20 adult insects were placed in contact with a sheet of filter paper which had been treated by placing 180 ml of an acetone solution of the test compound with a pipette on the paper. The contamination was effected 24 hours after treatment of the paper and the $DL_{50}$ was determined. The $DL_{50}$ for compound A was 0.75 mg/m².

D. Knock Down Activity against *Aedes Aegypti*

The test method was analogous to that described above for the lethal test except that the counting of the knocked down insects was determined at 2 minute intervals until all the insects were knocked down. After 4 minutes, 31.9% were dead, after 6 minutes 76.5% were dead and after about 8 minutes, 100% were dead with a dose of 83 mg of compound A per m².

E. Insecticidal Activity against *Aphis Craccivora*

A microdrop of an acetone solution of compound A was topically applied to *aphis Craccivora* and at the dose of 2 nanograms per insect, the mortality was 100% after 24 and 48 hours.

F. Insecticidal Activity against *Spodoptera Littoralis*

1 μl of an acetone solution of compound A was topically placed on the dorsal thorax of each insect using 15 *Spodoptera littoralis* caterpillars in the 4th larva stage for each dose. After this treatment, the individuals were placed in an artificial nutritive medium (Poitout medium) and the degree of efficacity was determined in nanogram per insect after 24 and 48 hours. At a dose of 10 nanograms of compound A per insect, 70% were dead after 24 hours and 100% were dead after 48 hours.

The test was repeated for compound B using *Epilachna Varivestris* instead of *Spodoptera littoralis* and the $DL_{50}$ was 4.5 nanograms per insect.

G. Insecticidal Activity against *Sitophilus Granarius*

Using the procedure of test F, an acetone solution of compound A was topically applied to *Sitophilus granarius* and the insects were then placed in wheat. The mortality was determined 24 and 48 hours and 6 and 7 days after treatment and at a dose of 20 nanograms of compound A per insect, 100% of the insects were dead after 24 hours.

From the above tests, it is concluded that compounds A and B have interesting insecticidal activity.

Various modifications of the compounds and methods of the invention may be made without departing from the spirit or scope thereof and it is to be understood that the invention is intended to be limited only as defined in the appended claims.

We claim:

1. An alcohol in the S form, R form or racemic mixtures thereof of the formula

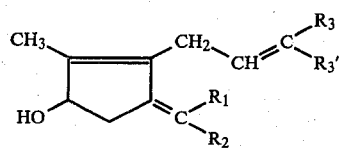

wherein $R_1$ and $R_2$ are individually selected from the group consisting of hydrogen, halogen, alkyl of 1 to 6 carbon atoms, phenyl, naphthyl, phenylalkyl of 7 to 13 carbon atoms alkoxycarbonyl of 2 to 5 carbon atoms and —CN and $R_3$ and $R_3'$ are individually selected from the group consisting of hydrogen, alkyl of 1 to 3 carbon atoms and alkenyl of 2 to 3 carbon atoms.

2. A compound of claim 1 which is 1S-hydroxy-2-methyl-3-allyl-4-methylene-cyclopent-2-ene.

3. A compound of claim 1 which is 1S-hydroxy-2-methyl-3-allyl-4-dichloromethylene-cyclopent-2-ene.

4. A compound of claim 1 which is 1S-hydroxy-2-methyl-3-allyl-4-dicyanomethylene-cyclopent-2-ene.

5. A compound of claim 1 which is 1S-hydroxy-2-methyl-3-allyl-4-ethylidene-cyclopent-2-ene.

6. A compound of claim 1 which is 1S-hydroxy-2-methyl-3-allyl-4E-benzylidene-cyclopent-2-ene.

7. A compound of claim 1 which is 1S-hydroxy-2-methyl-3-allyl-4-fluoromethylene-cyclopent-2-ene.

8. A compound of claim 1 which is 1S-hydroxy-2-methyl-3-allyl-4-cyanomethylene-cyclopent-2-ene.

9. A compound of claim 1 which is 1S-hydroxy-2-methyl-3-allyl-4-(cyanoethoxycarbonyl)-methylene-cyclopent-2-ene.

10. A compound of claim 1 which is 1RS-hydroxy-2-methyl-3-(3-methyl-2-buten-1)-4-methylene-cyclopent-2-ene.

* * * * *